(12) United States Patent
Deck

(10) Patent No.: US 9,226,704 B2
(45) Date of Patent: *Jan. 5, 2016

(54) DEVICE AND METHOD FOR POSITIONING A BODY PART FOR FLUID ANALYSIS

(71) Applicant: Roche Diagnostics Care, Inc., Indianapolis, IN (US)

(72) Inventor: Frank Deck, Niederkirchen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 139 days.

This patent is subject to a terminal disclaimer.

(21) Appl. No.: 13/743,398

(22) Filed: Jan. 17, 2013

(65) Prior Publication Data

US 2013/0197335 A1     Aug. 1, 2013

Related U.S. Application Data

(63) Continuation of application No. 11/562,242, filed on Nov. 21, 2006, now Pat. No. 8,376,959, which is a continuation of application No. PCT/EP2005/005301, filed on May 14, 2005.

(30) Foreign Application Priority Data

May 21, 2004    (DE) .................... 10 2004 024 970

(51) Int. Cl.
*A61B 5/15*     (2006.01)
*A61B 5/145*    (2006.01)
(Continued)

(52) U.S. Cl.
CPC ......... *A61B 5/150068* (2013.01); *A61B 5/1411* (2013.01); *A61B 5/14532* (2013.01); *A61B 5/151* (2013.01); *A61B 5/157* (2013.01)

(58) Field of Classification Search
CPC .................................. A61B 5/150068
USPC ........... 600/573, 583; 606/181–185, 201–204
See application file for complete search history.

(56) References Cited

U.S. PATENT DOCUMENTS

| 4,781,680 | A | | 11/1988 | Redmond et al. | |
| 5,951,493 | A | * | 9/1999 | Douglas et al. | 600/583 |
| 5,962,826 | A | * | 10/1999 | Bassin | 200/81 H |

(Continued)

FOREIGN PATENT DOCUMENTS

| DE | 100 26 172 A1 | 11/2001 |
| DE | WO 02/100276 A1 | 12/2002 |

(Continued)

OTHER PUBLICATIONS

International Patent Application PCT/EP2005/005301 International Search Report mailed May 21, 2004.

*Primary Examiner* — Sean Dougherty
(74) *Attorney, Agent, or Firm* — Woodard Emhardt Moriarty McNett and Henry LLP

(57) ABSTRACT

A device and a method are disclosed for positioning a body part (16) on an analytical device (14) for body fluids includes a flexible compression element (24) for pressing against the body part (16) while increasing the pressure and a rigid support part (26) to hold the compression element (24) on a housing (12) of the analytical device (14). The compression element (24) has an engaging member (34) for the body part (16) which can be pressed into the housing (12) such that a withdrawal region (56) of the body part (16) is exposed in the interior (18) of the housing (12) in order to remove liquid.

18 Claims, 4 Drawing Sheets

(51) Int. Cl.
*A61B 5/151* (2006.01)
*A61B 5/157* (2006.01)

(56) References Cited

U.S. PATENT DOCUMENTS

| | | | |
|---|---|---|---|
| 5,964,718 A | 10/1999 | Duchon et al. | |
| 6,121,559 A * | 9/2000 | Bassin | 200/81 H |
| 6,485,474 B1 | 11/2002 | Heinz et al. | |
| 6,503,210 B1 * | 1/2003 | Hirao et al. | 600/576 |
| 6,589,260 B1 * | 7/2003 | Schmelzeisen-Redeker et al. | 606/181 |
| 6,679,852 B1 * | 1/2004 | Schmelzeisen-Redeker et al. | 600/583 |
| 8,376,959 B2 * | 2/2013 | Deck | 600/573 |
| 2002/0188224 A1 * | 12/2002 | Roe et al. | 600/584 |
| 2006/0173380 A1 * | 8/2006 | Hoenes et al. | 600/583 |
| 2006/0184189 A1 * | 8/2006 | Olson et al. | 606/181 |

FOREIGN PATENT DOCUMENTS

| | | |
|---|---|---|
| DE | 198 24 238 A1 | 6/2005 |
| WO | WO 98/24366 A1 | 6/1998 |
| WO | WO 01/89383 A2 | 11/2001 |
| WO | WO 02/100274 A1 | 12/2002 |
| WO | WO 2005006985 A2 * | 1/2005 |

* cited by examiner

DEVICE AND METHOD FOR POSITIONING A BODY PART FOR FLUID ANALYSIS

CROSS-REFERENCE TO RELATED APPLICATION

This application is a continuation of U.S. patent application Ser. No. 11/562,242 filed Nov. 21, 2006, which is a continuation of International Application No. PCT/EP2005/005301 filed May 14, 2005, which claims benefit to German Patent Application 10 2004 024 970.9 filed May 21, 2004, all of which are hereby incorporated by reference.

FIELD OF THE INVENTION

The invention concerns a device and a method for positioning a body part, in particular a finger pad on an analytical device for body fluids and an appropriate analytical device according to the preamble of the independent patent claims.

BACKGROUND

A system for withdrawing body fluid is known from DE 100 26 172 A1 in which a deformable double cone is used as a compression unit to increase the inner pressure in a region of the pressed body part. In this process the downward pressure is partially converted into a movement in a secondary direction with a component at right angles to the primary direction until the upper and lower cone region rest against one another. In this state the constriction which ties off the body part is located above the plate-like support member whereas the puncture or blood removal site still lies within the collapsed double cone. This requires a point access for blood withdrawal with the risk that excess blood can contaminate the device. Moreover, the body part can accidentally slip if the coefficient of friction between the compression unit and the skin falls below a lower limit for example due to skin sweat or fat deposits. In this case a malfunction can also occur if the compression unit completely folds through into the inside of the device.

SUMMARY

Starting from this the object of the invention is to avoid the disadvantages occurring in the prior art and to improve a positioning device and an appropriate method such that a body part can be positioned in a reliable and defined manner free of interfering contours for an especially planar liquid removal using simple means.

The combination of features stated in the independent patent claims is proposed to achieve this object. Advantageous embodiments and further developments of the invention result from the dependent claims.

The invention is based on the idea of ensuring the body part is pressed as far as possible into the interior of the device. Accordingly the invention proposes that the compression element has an engaging member for the body part which can be pressed into the housing such that a withdrawal region of the body part is exposed in the interior of the housing opposite to a flat test field in order to remove liquid. In this manner the free space in the interior of the device can be used to apply liquid to a flat substrate without requiring a liquid transport for example by means of a capillary structure. The withdrawal below the edges of the housing allows a hygienic measurement process with small amounts of liquid (blood or tissue fluid) while the low lying engaging member ensures a stationary positioning. Moreover, a high positioning tolerance results from the flat uptake on the test field.

The engaging member can advantageously be pressed in up to the plane of a boundary of the support part on the housing such that the protruding or pinched off region of the body part is freely accessible.

For a further improvement of the positioning accuracy stop means are provided to limit the pressing depth of the compression element.

A special aspect of the invention is that the compression element that has a circular cross-section has a free outer edge that is widened by an outwardly projecting stop bead. Thus a stop situation is achieved when it is pressed inwards which reliably prevents a further inversion of the compression element.

An advantageous embodiment provides that the compression element has two subregions which converge in a conical manner towards the pressure axis wherein the distal subregion has a stop bead on its outside which abuts against the proximal subregion when it is pressed against the body part. In order to ensure that it is reliably stopped it is advantageous when the stop bead tapers preferably in a wedge-like manner away from the free outer edge of the compression element.

Alternatively or in addition thereto it is also possible that the support part has an opening to press in the compression element and that on the housing side an abutment extending into the area of the opening is attached to the support part in order to limit the depth of impression of the compression element. For a secure support it is advantageous when the abutment is formed by a stop ring which tapers into the opening of the support part.

In order to engage as deeply as possible it is advantageous when the compression element is permanently connected to a rim of the opening in the support part wherein the connecting area extends over the entire height of the opening rim so that it is pushed in as deeply as possible in the housing region during compression.

In order to optimize the force introduction it is advantageous when the area connecting the support part and compression element is inclined away from a boundary surface of the support part on the housing where the angle between the incline and the boundary surface should be in the range of 50° to 70°, preferably 60°.

For the compression process it is also advantageous when the compression element in the initial state has an inner surface which tapers in a kink-free manner towards a lateral edge of the support part on the housing.

In order to improve the fit to a curved contour of the body part and to secure the adhesion it is advantageous when the engaging member is formed by the inner edge of a concavely curved ring surface of the compression element.

For the manufacture it is advantageous when the compression element is moulded as a moulded part preferably as an injection moulded part onto the prefabricated support part. In this connection the compression element can be attached to the support part by an adhesive bond and in particular are formed by a primer.

The compression element is advantageously composed of silicon, rubber or polyurethane. Silicon is preferably used for hygienic reasons.

In a constructionally advantageous embodiment the support part is constructed as a dimensionally stable ring washer and especially one made of metal. A one-step manufacture can be achieved by designing the compression element consisting of a thermoplastic elastomer and the support part consisting of plastic as a two component injection moulded part.

In order to allow an exchange for example to fit it to the size of the body part or for cleaning, the support part can be inserted into a housing receiving member in a detachable manner.

For a compact design of a portable device it is advantageous when the total width of the support part perpendicular to the pressing direction is less than 25 mm, preferably less than 20 mm.

Another aspect of the invention concerns an analytical device for body fluids and in particular for determining blood sugar comprising a housing and a device for positioning a body part, in particular a finger pad, comprising a preferably circular flexible compression element for pressing against the body part while increasing the pressure and a rigid support part to hold the compression element on the housing. It is proposed according to the invention that the compression element has an engaging member for the body part which can be pressed into the housing such that a withdrawal region of the body part is exposed in the interior of the housing opposite to a flat test field in order to remove liquid. This allows the previously described advantages to be realized in a compact portable device.

For storage purposes a test tape is preferably arranged in the interior of the housing which has a plurality of test fields on a windable support tape. In addition a lancing device for insertion into the withdrawal region of the body part and an analytical device for detecting an analyte on a test field to which body fluid has been applied are arranged in the interior of the housing for an integrated system.

The test fields arranged consecutively on the test tape that is preferably located in a cassette can advantageously be moved successively into an active position with regard to the withdrawal region of the body part, the lancing device and/or the analytical device by means of a tape transport device.

A further simplification is achieved by the fact that the lancing device has a distal pressing face to press a test field against the withdrawal region of the body part.

In order to make the uptake of liquid more tolerant of position especially in the case of small amounts, it is particularly advantageous when the receiving area of the test field to which body fluid can be applied is more than 2×5 mm 2, preferably about 5×20 mm 2.

With regard to the process the object mentioned above is achieved in that the body part protrudes into the housing when it is pressed whereby a withdrawal region of the body part is kept free in the interior of the housing opposite to a flat test field for liquid withdrawal.

In order to further improve the user friendliness it is advantageous when body fluid on the exposed withdrawal region of the body part is applied to test fields stored on a test tape in the interior of the housing.

In order to integrate the individual analytical steps, a lancing device is inserted into the withdrawal region in the interior of the housing whereby body fluid dammed up under the increased inner pressure emerges from the generated puncture wound. In this connection it is advantageous when the lancing device and the test tape are removed from the withdrawal region of the body part during a phase of liquid efflux.

The test tape that is preferably wound up in a cassette is advantageously advanced such that an unused test field is moved to an active position relative to the withdrawal region of the body part.

Another simplification of the process is achieved by applying body fluid that has escaped from the withdrawal region of the body part to a test field by a lateral excursion of the test tape.

The impression depth of the compression element is preferably limited by stop means.

It is also particularly advantageous when the compression element is held on the housing as a replaceable part in a removable manner by means of a rigid part of the support.

BRIEF DESCRIPTION OF THE DRAWINGS

The invention is further elucidated in the following on the basis of the embodiment examples shown schematically in the drawing.

DETAILED DESCRIPTION

Figure 1:
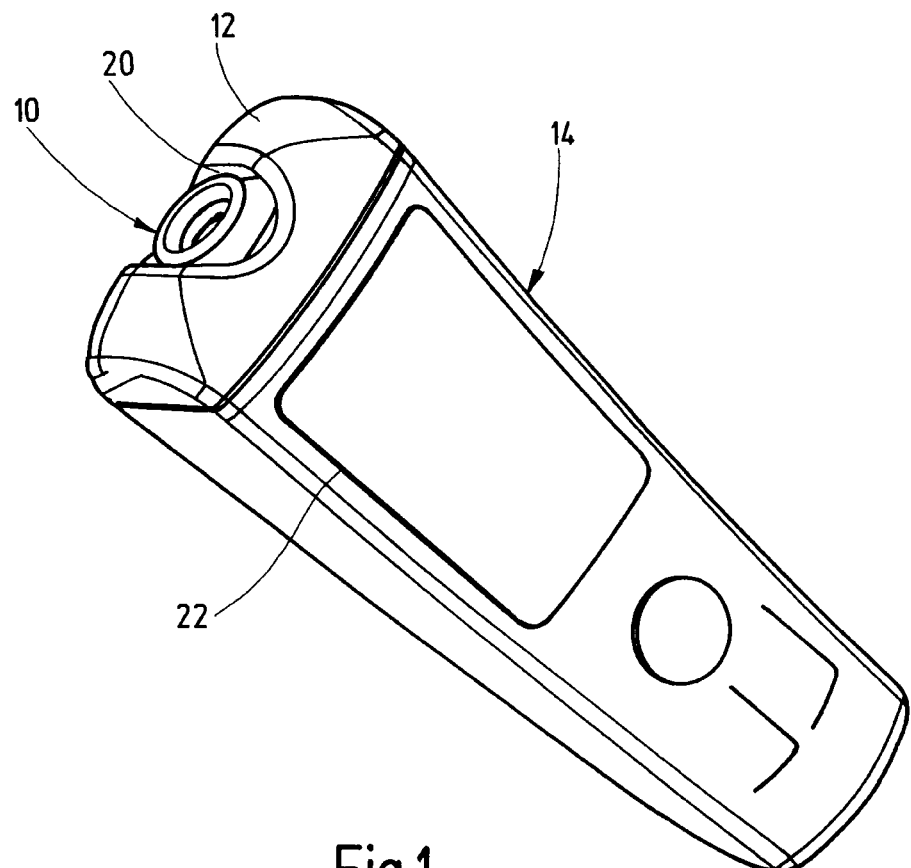
FIG. 1 shows a portable analytical device for determining blood sugar comprising a device for positioning a finger in a perspective view.

The positioning device 10 shown in the drawing can be inserted into the housing 12 of a portable blood sugar measuring instrument 14 as an easily exchangeable inserted part in order to position a finger pad 16 of a test person in the interior of the instrument 18 for blood withdrawal and analysis.

For this purpose the portable device 14 shown in FIG. 1 has a receiving member 20 for the exchangeable positioning device 10. The device as an integrated system comprises a lancing device 11 inside the instrument to puncture the finger pad and an analytical device 13 for determining the sugar content of the blood withdrawn at the puncture site (FIG. 6). The result that is determined can be shown to the user by a display unit 22.

Figure 2:
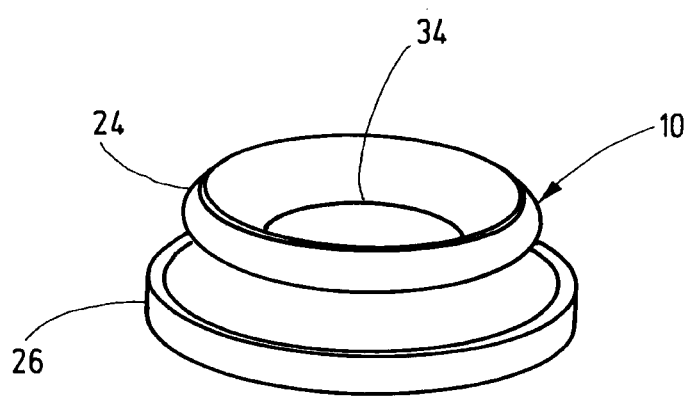
FIGS. 2 and 3 show the positioning device that can be removed from the instrument in a perspective view and in an axial section.
Figure 3:
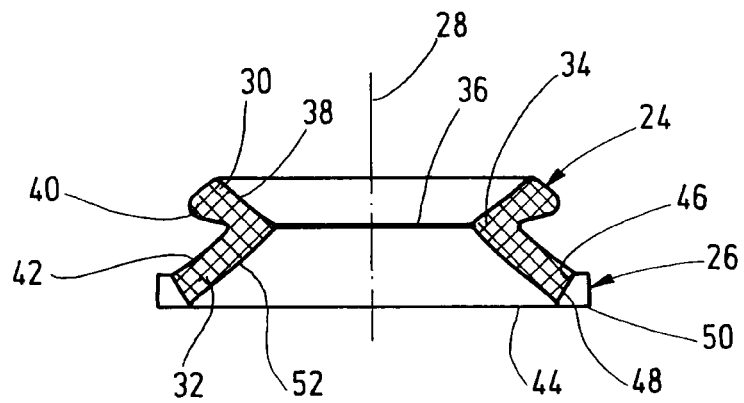

As best shown in FIGS. 2 and 3, the positioning device 10 has a flexible compression element 24 to press against the finger pad 16 and a dimensionally stable support part 26 to hold the compression element 24. The compression element 24 with a circular cross-section has two subregions 30, 32 which converge conically towards the pressure axis 28. The sharp bend between these subregions 30, 32 forms an open engaging member 34 to engage the finger pad 16 wherein the inner width in the area of the opening 36 is reduced during the pressing movement and thus squeezes the free finger tip while increasing the pressure in order to promote the accumulation of blood.

For a better match to the finger contour the upper or distal subregion 30 has a concavely curved inner ring surface 38. When the finger 16 is pressed on, this results firstly in a circular edge contact in the area of the engaging member 34 with a high face pressure for an antislip positioning.

In order to reliably stop the pressing movement, a stop bead 40 is moulded onto the free outer edge of the distal subregion 30 which tapers in a wedge-shaped manner towards the proximal subregion 32. In the stop position the stop bead 40 is braced against the outer side 42 of the subregion 32 and thus prevents further collapse of the compression element 24 in the pressing direction.

The support part 26 as a ring washer borders an opening 44 for the compression element 24. The support part 26 is permanently connected over its entire height and wall thickness to the rim of the opening 46 of the compression element 24 by means of an adhesive bond. For a favourable force introduction the connecting surface 48 is arranged as a slope at an acute angle of about 60° to the boundary surface 50 of the support part on the housing. In order to achieve a larger impression depth the inner surface 52 of the proximal subregion 32 extends with a smooth contour and without sharp bends towards the boundary edge of the rim of the opening 46 on the housing.

The compression unit 24 is made of silicon as a flexible moulded part whereas the support part 26 consists of metal and preferably aluminium. The compression element can be moulded onto the support part placed in an injection moulding tool in an injection moulding process where a primer on the contact area 48 increases the strength of the adhesive bond. Alternatively manufacture in a two-component injection moulding process is also conceivable in which the compression unit 24 is moulded from a thermoplastic elastomer and the support part 26 is moulded from plastic in one process step to form a composite part.

Figure 4:
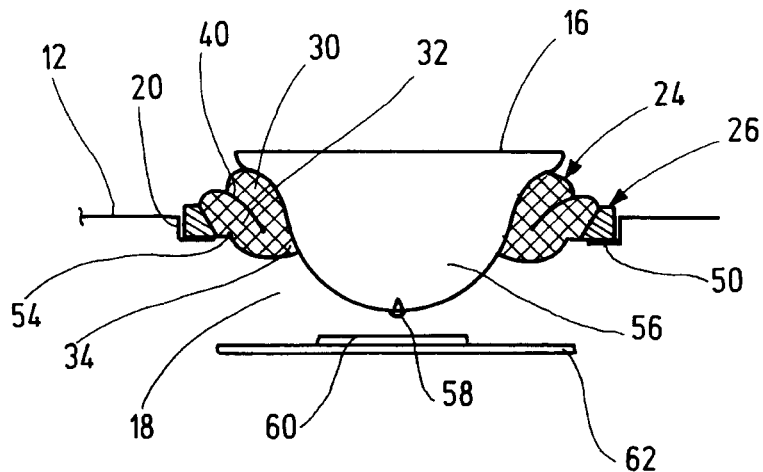
FIG. 4 shows the positioning device onto which a finger has been pressed for loading a test element in an axial section.

FIG. 4 shows the end or stop position of the compression unit 24 when the finger 16 is pressed on. The wedge-shaped stop bead 40 fills the outer interspace between the subregions 30, 32 without gaps such that complete collapse is prevented due to the incompressibility of the elastomer material even with a low coefficient of friction of the skin.

The bending site 54 is shifted downwards corresponding to the pressing direction due to the deep connection of the proximal subregion 32 to the rim of the opening 46. The engaging member 34 thus extends into the interior 18 of the housing 12 and in any case under the boundary surface 50 of the support part 26 on the housing. Accordingly a withdrawal region 56 of the finger pad 16 is exposed in the interior of the housing 18. After the puncture it is thus possible to remove an emerging drop of blood 58 freely by a flat test field 60 without requiring a point access. This type of automatic blood collection is particularly suitable in combination with a tape cassette system that can be used to transport a plurality of test fields 60 stored on a support tape 62 successively into the engaging region of the body part 16.

Figure 5:
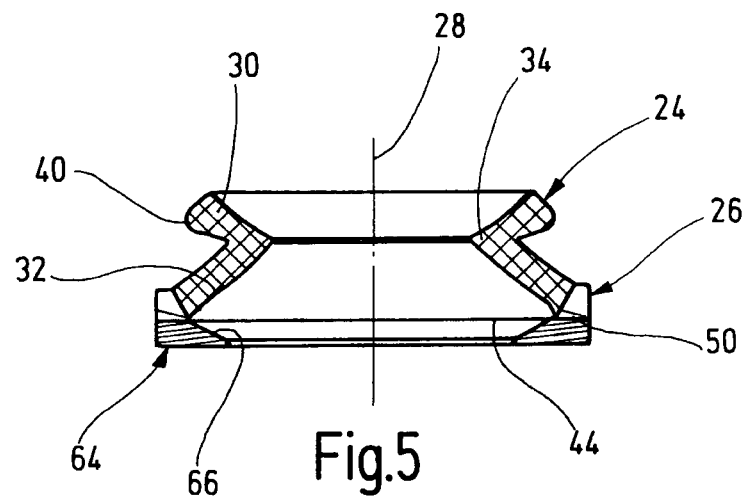
FIG. 5 shows another embodiment in a view corresponding to FIG. 3.

In the embodiment shown in FIG. 5 the same parts have the same reference numerals as described above. In addition an abutment 64 is provided which is attached to the face 50 of the support part 26 which borders the housing. The abutment 64 extends into the area of the opening 44 in order to limit the impression depth of the compression element 24. The abutment 64 in the area of the opening is bevelled downwards towards a free rim edge to form a stop face 66 for a form locking support that is bevelled in the opposite direction relative to the inner face 52 of the compression element 24. Thus an additional positioning accuracy of the finger tip 56 is achieved for blood withdrawal in the interior of the device.

FIG. 6a to e show the process of blood withdrawal and analysis in individual steps. In the device 14 the positioning device 10 is used as an exchangeable part whereas a test tape 70 and the lancing device 11 are located under it in the interior of the device 18. The test tape 70 has a plurality of test fields 60 which are arranged spaced apart in the tape direction on the carrier tape 62. The carrier tape 62 is provided with lancing openings 72 between the test fields 60 for the lancing element 74 that is pretensioned in the lancing device 11. The test tape 70 is advantageously wound onto spools (supply spool and waste spool) in a cassette that is not shown.

Figure 6A:
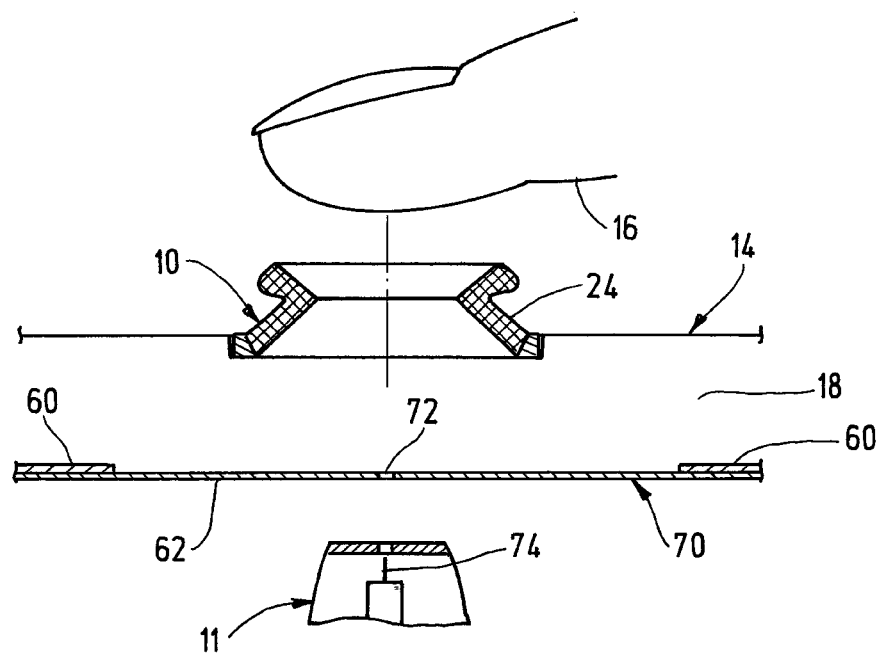
FIG. 6a to e show the process of blood withdrawal/analysis each in an axial section.
Figure 6B:
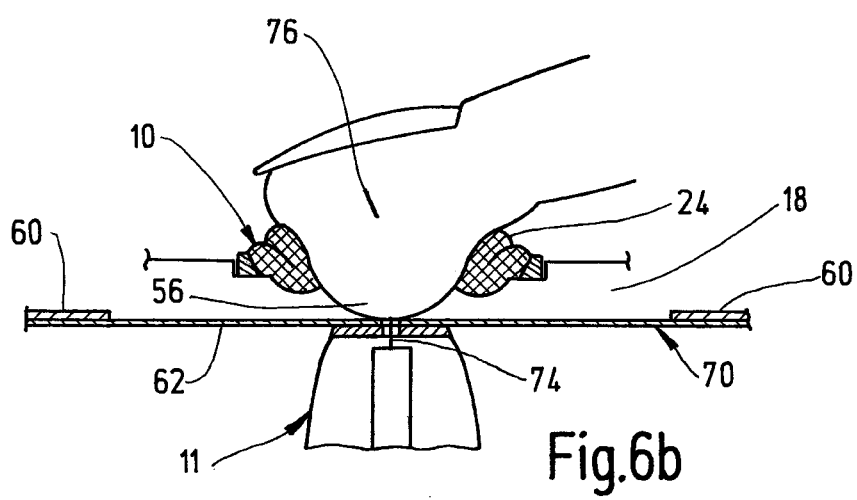
Figure 6C:
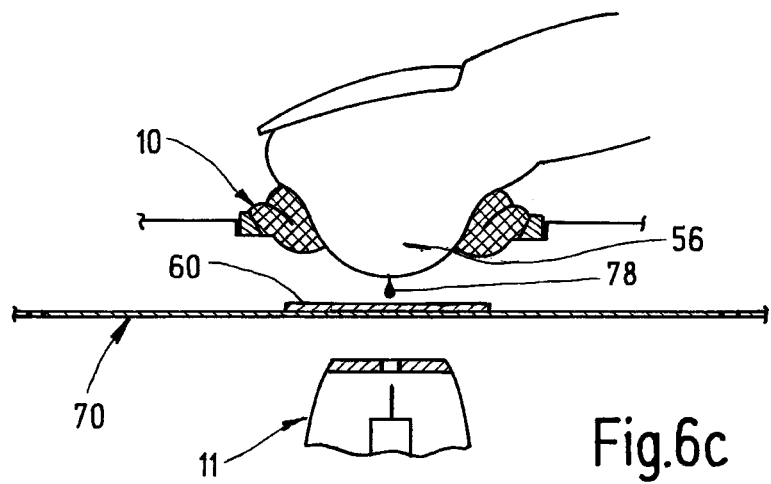

When the finger tip 16 is pressed against the compression element 24, the blood capillaries in the squeezed region of the finger 76 are tied off while the withdrawal region 56 is kept clear in the interior of the device 18 for blood withdrawal (FIG. 6b). For this purpose a puncture wound from which blood 78 can escape is generated by pushing the lancing element 74 forwards through the opening 72. In order not to impede the discharge of blood, the lancing device 11 and the test tape 70 are at a distance from the withdrawal region 56 during this phase that lasts a few seconds. The test tape 70 is positioned by winding on such that an unused test field 60 is moved opposite to the withdrawal region 56.

Figure 6D:
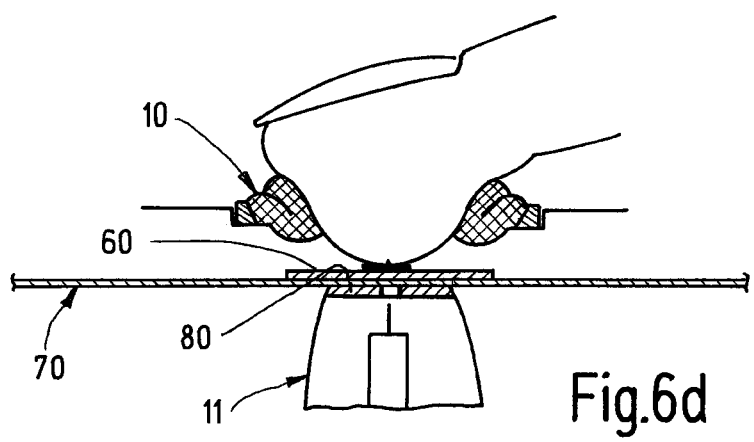

According to FIG. 6d the discharged drop of blood 78 is transferred directly onto the receiving area of the test field 60 by laterally deflecting the test tape 70 by a distal pressing face 80 of the lancing device 11 or by other means. Due to the dimensions of the area of the test element 60, the positioning relative to the puncture wound is very variable whereas the direct access for blood uptake or "dabbing" avoids a dead volume due to transport capillaries or such like.

Figure 6E:
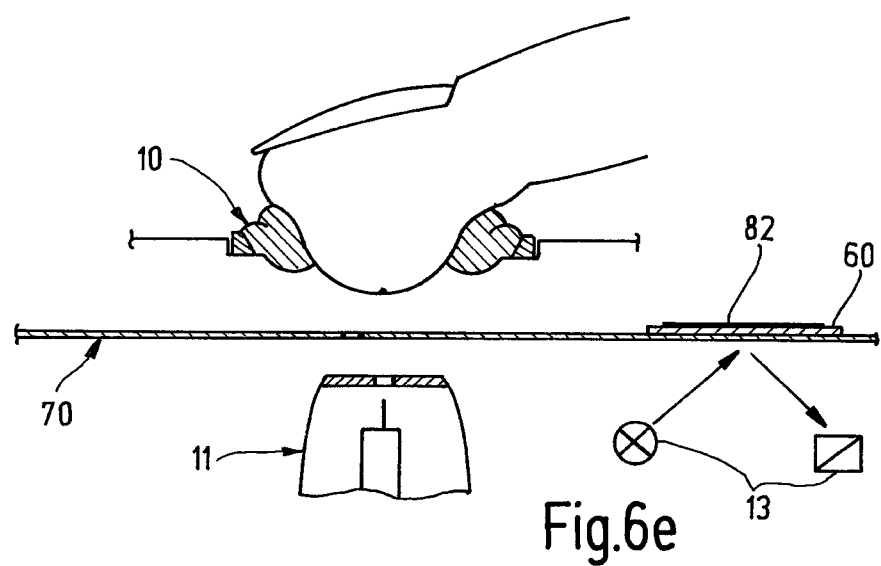

As shown in FIG. 6e the test field 60 with the applied blood 82 is transported by advancing the tape into the detection area of the optical analytical device 13. A test chemistry is disposed on the test field 60 which reacts with an analyte in this case glucose in the blood 82 for example with a colour change. This can be detected reflectometrically through the transparent carrier tape and be processed for display and/or storage of the measured glucose value. The used test field 60 is hygienically disposed off on the waste spool of the cassette while a fresh test field is provided again for the next measurement without the user having to reach into the device.

The invention claimed is:

1. A device for positioning a body part on an analytical device for body fluids, comprising:
    a flexible compression element for pressing against the body part while increasing pressure;
    a rigid support part to hold the compression element on a housing of the analytical device, wherein the support part has a bottom surface that faces an interior of the housing;
    wherein the compression element has an engaging member for the body part, wherein the compression element is configured to be pressed into the housing past the bottom surface of the support part such that a withdrawal region of the body part is exposed in the interior of the housing opposite to a flat test field in order to remove liquid; and
    wherein stop means are provided to limit a pressing depth of the compression element.

2. The device according to claim 1, characterized in that the engaging member can be pressed in at least up to a plane of a boundary of the support part on the housing.

3. The device according to claim 1, characterized in that the compression element has a free outer edge that is widened by an outwardly projecting stop bead, wherein the compression element has a circular cross section.

4. The device according to claim 1, characterized in that the compression element has a distal subregion and a proximal subregion which converge in a conical manner towards a pressure axis, wherein the distal subregion has a stop bead on an outside of the distal subregion which abuts against the proximal subregion when the distal subregion is pressed against the body part.

5. The device according to claim 3, characterized in that the stop bead tapers in a wedge-like manner away from a free outer edge of the compression element.

6. The device according to claim 1, characterized in that the compression element in an initial position has an inner surface which tapers in a kink-free manner towards a lateral edge of the support part on the housing.

7. The device according to claim 1, characterized in that the compression element has a moulded connection to the support part.

8. The device according to claim 1, characterized in that the compression element is composed of silicon, rubber or polyurethane.

9. The device according to claim 1, characterized in that the support part is constructed as a dimensionally stable ring washer.

10. The device according to claim 1, characterized in that the support part can be inserted into a housing receiving member in a detachable manner.

11. An analytical instrument for body fluids characterized by the device for positioning the body part according to claim 1.

12. An analytical instrument for body fluids, comprising:
    a housing;
    a device for positioning a body part including
        a flexible compression element for pressing against the body part while increasing pressure,
        a rigid support part to hold the compression element on the housing, wherein the support part has a bottom surface that faces an interior of the housing, and
        wherein the compression element has an engaging member for the body part configured to press into the housing during liquid withdrawal such that a withdrawal region of the body part is exposed past the bottom surface in the interior of the housing opposite to a flat test field; and
    a test tape arranged in an interior of the housing, wherein the test tape has a plurality of test fields on a windable support tape.

13. The analytical instrument according to claim 12, characterized in that the device has a distal pressing face to press a test field against the withdrawal region of the body part.

14. A method for analysing body fluids, comprising:
    positioning a body part on an analyser, wherein said positioning includes pressing the body part against a flexible compression element in order to increase internal pressure, wherein the compression element has an engaging member for the body part, wherein a support part has a bottom surface that faces an interior of a housing; and
    penetrating the body part into the housing past the bottom surface by pressing the compression element into the housing such that a withdrawal region of the body part is exposed in the interior of the housing opposite to a flat test field in order to remove liquid.

15. The method according to claim 14, characterized in that body fluid on the withdrawal region of the body part is applied to test fields stored on a test tape in the interior of the housing.

16. The method according to claim 14, characterized in that a lancing device is inserted into the withdrawal region in the interior of the housing whereby body fluid dammed up under the increased inner pressure emerges from a generated puncture wound.

17. The method according to claim 14, characterized in that an impression depth of the compression element is limited by stop means.

18. The method according to claim 14, characterized in that the compression element is held on the housing as a replaceable part in a removable manner by means of a rigid part of the support.

* * * * *

UNITED STATES PATENT AND TRADEMARK OFFICE
CERTIFICATE OF CORRECTION

PATENT NO.         : 9,226,704 B2
APPLICATION NO.    : 13/743398
DATED              : January 5, 2016
INVENTOR(S)        : Frank Deck Page 1 of 1

It is certified that error appears in the above-identified patent and that said Letters Patent is hereby corrected as shown below:

On the Title page, in item (71) Applicant: replace "Roche Diagnostics Care, Inc." with
--Roche Diabetes Care, Inc.--

Signed and Sealed this
Twenty-sixth Day of April, 2016

Michelle K. Lee
*Director of the United States Patent and Trademark Office*